United States Patent [19]

Habeck et al.

[11] 3,957,816

[45] May 18, 1976

[54] SUBSTITUTED NAPHTHO PYRAZOLES

[75] Inventors: Dietmar A. Habeck, Heidelberg, Germany; William J. Houlihan, Mountain Lakes, N.J.

[73] Assignee: Sandoz, Inc., E. Hanover, N.J.

[22] Filed: June 27, 1974

[21] Appl. No.: 483,626

Related U.S. Application Data

[62] Division of Ser. No. 328,402, Jan. 31, 1973, Pat. No. 3,842,088.

[52] U.S. Cl. .......................... 260/310 C; 260/310 R
[51] Int. Cl.$^2$ ........................................ C07D 231/54
[58] Field of Search .......... 260/310 R, 296 T, 310 C

[56] References Cited
UNITED STATES PATENTS 3,842,088  10/1974  Habeck et al. .................. 260/296 T

FOREIGN PATENTS OR APPLICATIONS 2,249,644  4/1973  Germany

OTHER PUBLICATIONS

Chemical Abstracts Vol. 80: 108438q (1974).

*Primary Examiner*—Donald B. Moyer
*Attorney, Agent, or Firm*—Gerald D. Sharkin; Robert S. Honor; Thomas O. McGovern

[57] ABSTRACT

Substituted naphtho [1,2-c] pyrazoles e.g., 4,5-dihydro-5-methyl-3-(4-pyridyl)-2H-naphtho[1,2-c]-pyrazole, are useful as non-estrogenic anti-fertility agents.

3 Claims, No Drawings

SUBSTITUTED NAPHTHO PYRAZOLES

This is a division of application Ser. No. 328,402 filed Jan. 31, 1973 which issued as U.S. Pat. No. 3,842,088, on Oct. 15, 1974.

This invention relates to naphtho [1,2-c] pyrazole derivatives. More particularly it relates to 3-phenyl and 3-pyridyl derivatives of 4 and/or 5 alkyl substituted naphtho [1,2-c] pyrazoles and their use in pharmaceutical compositions.

The compounds of this invention may be represented by the following formula:

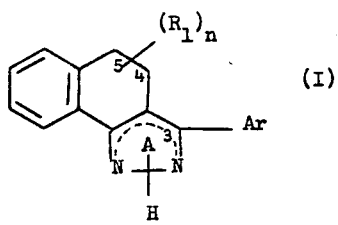

where
  n is 1 or 2,
  R₁ represents straight-chain lower alkyl having 1 to 4 carbon atoms, e.g., methyl, ethyl, propyl, and the like and
  Ar is

 or 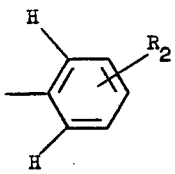

where R₂ represents hydrogen or halo having an atomic weight of about 19 to 36,
and pharmaceutically acceptable acid addition salts thereof.

The pyrazole ring (A) in the compounds of formula (I) can have the following structures:

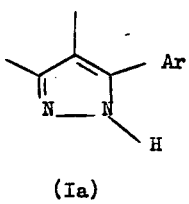 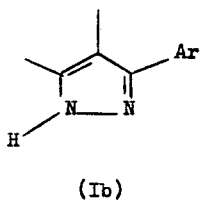

(Ia)  (Ib)

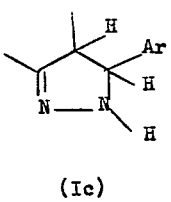

(Ic)

It should be noted that the compounds of structures (Ia) and (Ib) are considered equivalent and are known to exist in both tautomeric forms. It should be noted that this invention includes the geometrical and optical isomers of the compounds of structures (Ic).

The compounds of formula (I) in which ring A has the structure (Ia) and (Ib) may be prepared by the following reaction scheme:

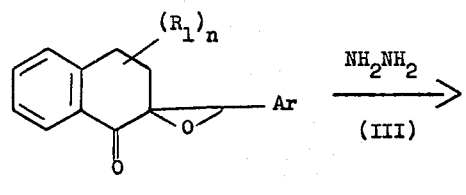

(II)

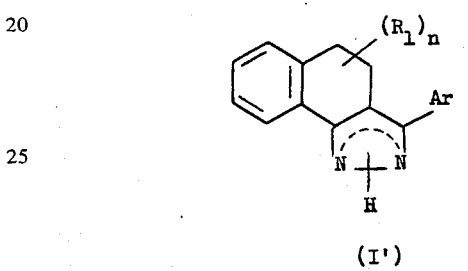

(I')

where n, R₁, and Ar are as set out above.

The compounds of formula (I') are prepared by treating a compound of formula (II) with hydrazine of formula (III). The reaction is preferably carried out under acidic catalysis which can be provided by a mineral acid such as hydrochloric acid, sulfuric acid, and the like, an organic acid such as acetic acid and the like or a Lewis acid such as boron trifluoride and the like. The preferred acids are acetic acid and boron trifluoride. Although a solvent is not required, it is preferred that the reaction be carried out in the presence of an inert solvent such as alkanols having 1 to 4 carbon atoms, aliphatic or aromatic hydrocarbons, halogenated hydrocarbons, straight chain ethers or cyclic ethers. The particular solvent used is not critical, but the alkanols, such as methanol, ethanol, and the like or dioxane are preferred. The temperature of the reaction also is not critical but it is generally carried out between 35° and 200°C preferably at the reflux temperature of the system. It is also preferred that the reaction be run for from 8 hours to 5 days. The product is recovered in the usual manner, e.g., by evaporation and crystallization.

The compounds of formula (Ic) can also be prepared by the following reaction scheme:

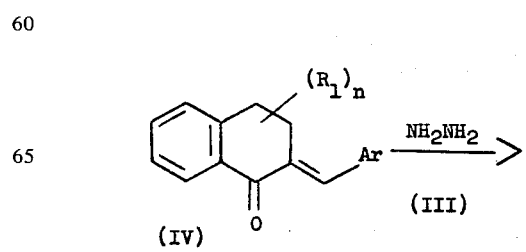

(IV)

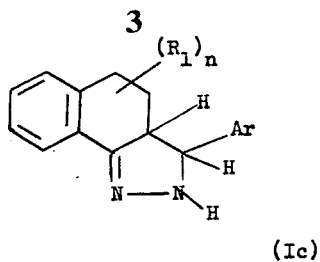

(Ic)

where $n$, $R_1$ and Ar are as set out above.

The compounds of formula (Ic) are prepared by treating a compound of formula (IV) with hydrazine of formula (III). Although a solvent is not necessary, it is preferred that the reaction be carried out in an inert solvent such as alkanols having 1 to 4 carbon atoms, aliphatic or aromatic hydrocarbons, halogenated hydrocarbons, straight chain ethers or cyclic ethers. The particular solvent used is not critical but the preferred solvents are the alkanols such as methanol, ethanol, butanol and the like. The temperature of the reaction is not critical, but it is normally carried out between 35° and 150°C preferably at the reflux temperature of the system. It is also preferred that the reaction be run for from 8 hours to 5 days under anhydrous conditions. When the preceeding reaction is carried out in an inert atmosphere, such as helium, argon or nitrogen, the compound with structure (Ic) is predominantly obtained and is isolated by conventional techniques, e.g., chromatography.

The compounds of formulas (Ia) and (Ib) can be prepared by the following reaction from the compounds of formula (Ic):

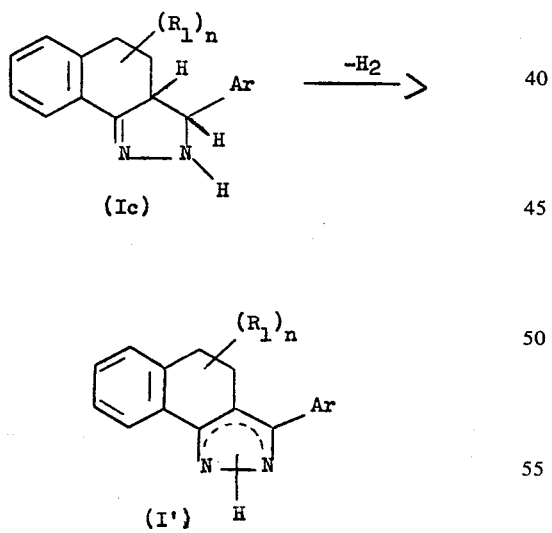

where $n$, $R_1$ and Ar are as set out above.

The compounds of formula (I') are prepared by dehydrogenating a compound of formula (Ic). The dehydrogenation can be carried out by exposing compound (Ic) to oxygen for example on a chromatographic media such as silica or alumina. Alternately, the reaction may be carried out in the presence of a dehydrogenating agent such as sulfur or palladium or an oxidizing agent such as manganese dioxide or lead dioxide plus acid. Although a solvent is not essential in the reaction and the temperature is not critical, it is preferred that an inert solvent be used and that the reaction be carried out between temperatures of 20° to 250°C. When sulfur or palladium is used as the dehydrogenation agent, the preferred solvents are decalin, xylene, naphthalene and the like and the preferred temperature is 200° to 250°C. With manganese dioxide, the preferred solvent is benzene, toluene and the like, and the preferred temperature is 20° to 50°C. When lead dioxide and acetic acid are used in the reaction, the preferred solvent is excess acetic acid and the preferred temperature of the reaction is 20° to 50°C. It is further preferred that the reaction be run for 5 to 50 hours, especially from 5 to 25 hours. The products are recovered by conventional techniques, e.g., evaporation and recrystallization.

The compounds of formulas (Ia) and (Ib) may also be prepared by the following reaction scheme:

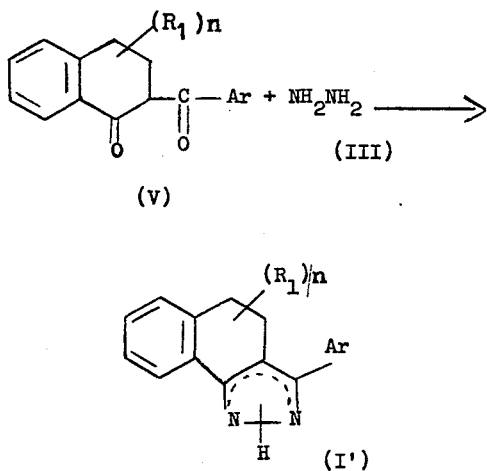

where $n$, $R_1$ and Ar are as set out above.

The compounds of formula (I') are prepared by treating a compound of the formula (V) with hydrazine of formula (III). Although a solvent is not necessary, it is preferred that the reaction be carried out in an inert solvent such as alkanols having 1 to 4 carbon atoms, e.g., ethanol, ethers, e.g., diethyl ether, dioxane or tetrahydrofuran, halogenated hydrocarbons such as chloroform, or in excess hydrazine of formula (III). The temperature of the reaction is not critical, but the reaction is preferably run at between 30° to 150°C, especially at the reflux temperature of the reaction mixture. The product is isolated by standard techniques, e.g., recrystallization.

The compounds of formula (II) are prepared in accordance with the following reaction scheme:

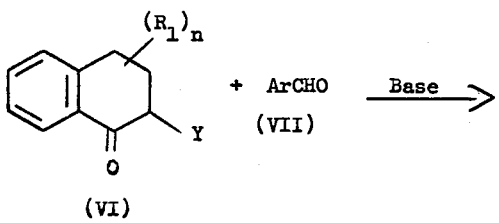

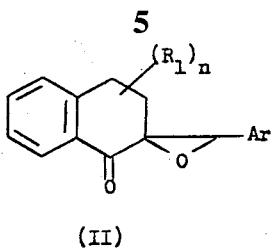

(II)

where
Y is a leaving group and
$n$, $R_1$, and Ar are as set out above.

The compounds of formula (II) are prepared by treating the compounds of formula (VI) with the compounds of formula (VII) under basic conditions in an inert solvent. It is preferred that the reaction be run in an inert atmosphere such as argon, helium and especially nitrogen. The leaving group Y in formula (VI) can be any of the conventional leaving groups employed in such a reaction, such as chlorine, bromine, iodine, tosylate, mesylate and the like. The preferred leaving group is a halogen especially chlorine or bromine. The basic conditions for the reaction are provided by alkali or alkali earth metal hydroxides, alkali metal lower alkoxides, tertiary aliphatic and aromatic amines and tertiary cyclic amines such as pyridine and the like. Although the particular solvent used is not critical, the alkanols such as methanol, ethanol, butanol, and the like are especially preferred, in particular the alkanol corresponding to the alkali metal alkoxide when used. The temperature of the reaction is not critical, but is is generally carried out between 0° to 30°C preferably about 5° to 10°C. Although the time is not critical, it is preferred that the reaction be run for from 1 to 5 hours. The product is recovered by standard techniques e.g., by crystallization or distillation.

The compounds of formula (II) can also be prepared by the following reaction scheme:

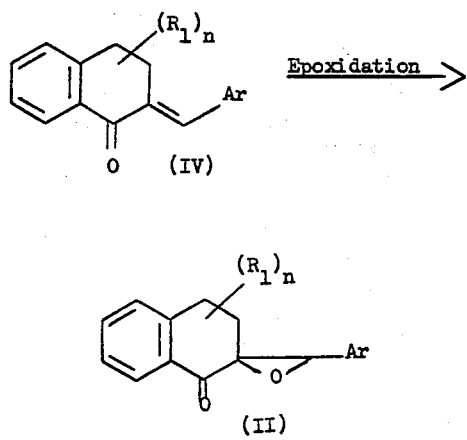

where $n$, $R_1$ and Ar are as set out above.

The compounds of formula (II) are prepared by treating the compounds of formula (IV) with an epoxidizing agent in an inert solvent. The epoxiding agent used can be any of the standard expoxidizing agents used in epoxidizing α,b-unsaturated ketones, e.g., hydrogen peroxide and bases such as the alkali metal hydroxides or alkoxides. The inert solvent can be water, alkanols having 1 to 4 carbon atoms, aliphatic or aromatic hydrocarbons, halogenated hydrocarbons, straight chain ethers, cyclic ethers, and the like depending on the solubility characteristics of the reactants, in particular, the epoxidizing agents. The preferred solvents are water and the alkanols such as methanol, ethanol, butanol and the like. The temperature of the reaction is not critical, but it is normally carried out between 0° and 100°C, depending on the epoxidizing agent but preferably between 15° to 30°C. It also preferred that the reaction be run from 3 hours to 2 days preferably 5 to 10 hours. The product is recovered in the usual manner, e.g., by extraction and evaporation.

The compounds of formulas (IV) and (VI) are prepared by well known procedures from compounds of the formula:

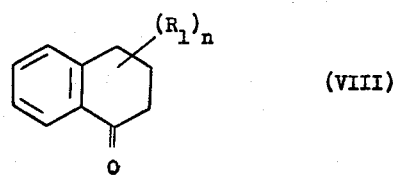

where $n$ $R_1$ are as set out above.

The compounds of formula (IV) are, for example, prepared by treating a compound of formula (VIII) with a compound of formula (VII). The process is suitably carried out by standard techniques, preferably in an inert solvent such as ethanol, and in the presence of a catalytic amount of a base such as sodium hydroxide, potassium hydroxide, diethylamine, or triethylamine or in the presence of a catalytic amount of an acid such as hydrochloric acid, sulfuric acid, phosphoric acid, acetic acid, toluene-sulfonic acid or methylsulfonic acid. The temperature of the reaction is 15° to 100°, and the reaction is run for from 2 to 24 hours. The particular solvent, temperature or time used in the reaction is not critical.

The compounds of formula (VI) may be obtained by standard procedure from compounds of formula (VIII). For example, the chlorine or bromine substituted compounds can be prepared by treating the compound of formula (VIII) with chlorine or bromine, preferably in an inert solvent such as acetic acid, chloroform or carbon tetrachloride. The reaction can be carried out at temperatures from room temperature to 50° over a period of 1 to 12 hours.

The tosylate and mesylate can be prepared from the chlorine or bromine substituted compound by treatment with a tosylate or mesylate salt, such as sodium or potassium tosylate or mesylate in an inert solvent such as alcohols having 1 to 4 carbon atoms, toluene or benzene. The reaction is preferably carried out at temperatures between 15° to 70° for a period of from 2 to 10 hours.

The hydrazine of formula (III) and many of the compounds of formula (V), (VII) and (VIII) are known and are prepared by procedures disclosed in the literature. The compounds of formula (V), (VII) and (VIII) not specifically disclosed in the literature may be prepared by analgous methods using known starting materials.

The compounds of formula (I) are useful because they possess pharmacological activity in animals. In particular, the compounds are useful as anti-fertility agents as indicated by their activity in female Wistar rats which are injected daily with 2 mg of the compound for eight successive days starting on the day of vaginal cornification. At the time of the 4th injection, males of known fertility are cohabitated with the females (one female with one male) until the end of the treatment period. The males are separated from the females 24 hours following the last injection. The females are sacrificed 6 days later, and examined for the presence of absence of implantation sites.

The use of the compound as anti-fertility agents is further indicated by their luteolytic properties which results in the compounds being abortifacient agents. The luteolytic activity is determined using pseudopregnant rabbits treated with corn oil or compound (1 –100 mg per day) suspended in corn oil on days 3 through 8 of pseudopregnancy. Blood samples are obtained daily throughout the length of pseudopregnancy. Plasma samples are analyzed for progestin content according to the method of Johansson et al. (Endocrinology 82, 143, 1968). The compound is judged active if plasma progestin levels are similar to pretreatment values on day 12 of pseudopregnancy.

Abortifacient activity is also determined in female proestrous rats (Royal Hart, Wistar strain) selected from a colony and caged with fertile males. On the following day pregnancy is confirmed by the presence of spermatozoa in the viginal smear. On the seventh day following mating the females are treated with 1 to 30 milligrams of the compound to be tested. The animals are injected daily for a total of 7 days; and on the eighth day following the first injection the animals are killed and the uterus checked for the presence of absence of implantation sites.

The compounds of formula (I), when used as anti-fertility agents exhibit none of the estrogenic effects and side effects exhibited by the steroidal type compounds used for these purposes.

When the compounds are employed for the above utility, they may be combined with one or more pharmaceutically acceptable carriers or adjuvants, and may be administered orally in such forms as tablets, capsules, elixirs, suspensions and the like, bucally or subligually as a tablet, parenterally in the form of an injectable solution or suspension or in special forms such as suppositories and the like especially pessaries. Depending upon the compound employed and the mode of administration the exact dosage utilized may vary.

Furthermore, the compounds of formula (I) may be similarly administered in the form of their non-toxic pharmaceutically acceptable acid addition salts. Such salts possess the same order of activity as the free base, are readily prepared by reacting the base with an appropriate acid and accordingly, are included within the scope of the invention. Representative of the acid addition salts are the mineral acid salts, such as the hydrochloride, hydrobromide, sulfate, phosphate and the like and the organic acid salts, such as the succinate, benzoate, acetate, p-toluenesulfonate, benzenesulfonate, and the like.

In general, satisfactory results are obtained when the compounds of formula (I) are administered as anti-fertility agents at a daily dosage of about 1.0 milligrams to about 200 milligrams orally or subcutaneously per kilogram of animal body weight. This daily dosage is preferably administered 1 to 4 times a day or in sustained release form. For most large mammals, such as primates, the total daily dosage is from about 1 milligram to about 1 gram. Dosage forms suitable for internal use comprise from about 0.25 milligrams to about 0.5 grams of the active compound in intimate admixture with a solid or liquid pharmaceutically acceptable carrier or diluent.

A representative formulation suitable for oral administration 2 to 4 times a day in fertility control is a capsule prepared by standard encapsulating techniques which contain the following.

| Ingredients | Weight (mg) |
|---|---|
| 4,5-dihydro-5-methyl-(4-pyridyl)-2H-naphtho [1,2-c] pyrazole | 100 |
| Inert solid diluent (starch, lactose, kaolin) | 200 |

EXAMPLE 1

4,5-dihydro-5-methyl-3-(4-pyridyl)-2H -naphtho [1,2-c]pyrozole

Step A: 3'-(4-pyridyl)-spiro[4-methyl-1,2,3,4-tetrahydronaphthalene-2,2'-oxirane]-1-one To a stirred solution of 22.4 grams of 2-bromo-4-methyl-$\alpha$-tetralone and 10.1 grams of pyridine-4-carboxaldehyde in 50 ml. of methanol under nitrogen is added at 5° to 10°C, a solution of sodium methoxide in methanol (prepared by dissolving 2.2g. of sodium in 150 ml methanol). After 2 hours, 3'-(4-pyridyl)-spiro[4-methyl-1,2,3,4-tetrahydronaphthalene-2,2'-oxirane]-1-one precipitates and is filtered off and recrystallized from methanol, m.p. 138°–140°.

When an equivalent amount of
a. 2-bromo-3-methyl-$\alpha$-tetralone;
b. 2-bromo-3,4-dimethyl-$\alpha$-tetralone or
c. 2-bromo-4,4-dimethyl-$\alpha$-tetralone is used in place of the 2-bromo-4-methyl-$\alpha$-tetralone above there is obtained a.     3'-(4-pyridyl)-spiro[3-methyl-1,2,3,4-tetrahydronaphthalene-2,2'-oxirane]-1-one,
b. 3'-(4-pyridyl)-spiro[3,4-dimethyl-1,2,3,4-tetrahydronaphthalene-2,2'-oxirane]-1-one or
c. 3'-(4-pyridyl)-spiro[4,4-dimethyl-1,2,3,4-tetrahydronaphthalene-2,2'-oxirane]-1-one respectively.

When an equivalent amount of p-chlorobenzaldehyde or benzaldehyde is used in place of the pyridine-4-carboxaldehyde above, there is obtained 3'-(p-chlorophenyl)-spiro[4-methyl-1,2,3,4-tetrahydronaphthalene-2,2'-oxirane]-1-one or 3'-phenyl-spiro[4-methyl-1,2,3,4-tetrahydronaphthalene-2,2'-oxirane]-1-one respectively.

Step B: 4,5-dihydro-5-methyl-3-(4-pyridyl)-2H-naphtho 1,2-c]pyrazole

A mixture of 7.4 grams of 3'-(4-pyridyl)-spiro[4-methyl-1,2,3,4-tetrahydronaphthalene-2,2'-oxirane]-1-one from Step A, 4.5 ml. of 7% hydrazine 8.4g acetic acid, 40.0 ml. of ethanol and 50 ml of dioxane are refluxed for 12 hours. On cooling the mixture, 4,5-dihydro-5-methyl-3-(4-pyridyl)-2H-naphtho[1,2-c]pyrazole precipitates and is recovered by filtration.

The 4,5-dihydro-5-methyl-3-(4-pyridyl)-2H-naphtho [1,2-c]pyrazole of this example is an effective fertility control agent when it is subcutaneously administered to an animal at a dosage of 100 milligrams two times a day.

Following the above procedure, but using an equivalent amount of a. 3'-(4-pyridyl)-spiro[3-methyl-1,2,3,4-tetrahydronaphthalene-2,2-oxirane]-1-one;
b. 3'-(4-pyridyl)-spiro[3,4-dimethyl-1,2,3,4-tetrahydronaphthalene-2,2'-oxirane]-1one;
c. 3'-(4-pyridyl)-spiro[4,4-dimethyl-1,2,3,4-tetrahydronaphthalene-2,2'-oxirane]-1-one;
d. 3'-(p-chlorophenyl)-spiro[4-methyl-1,2,3,4-tetrahydronaphthalene-2,2'-oxirane]-1-one or
e. 3'-phenyl-spiro[4-methyl-1,2,3,4-tetrahydronaphthalene-2,2'-oxirane]-1-one in place of the 3'-(4-pyridyl)-spiro [4-methyl-1,2,3,4-tetrahydronaphthalene-2,2'-oxirane]-1-one used therein, there is obtained.
  a. 4,5-dihydro-4-methyl-3-(4-pyridyl)-2H-naphtho[1,2-c]pyrazole;
  b. 4,5-dihydro-4,5-dimethyl-3-(4-pyridyl)-2H-naphtho[1,2-c]pyrazole;
  c. 4,5-dihydro-5,5-dimethyl-3-(4-pyridyl)-2H-naphtho[1,2-c]pyrazole or
  d. 4,5-dihydro-5-methyl-3-(p-chlorophenyl)-2H-naphtho[1,2-c]pyrazole
  e. 4,5-dihydro-5-methyl-3-phenyl-2H-naphtho[1,2-c]pyrazole respectively.

EXAMPLE 2

4,5-dihydro-5-methyl-3-(4-pyridyl)-2H-naphtho[1,2-c]pyrazole

To a mixture of 10 grams of 2-(4-pyridylmethylene)-3,4-dihydro-4-methyl-1(2H)-naphthalenone in 100 ml. of water and 200 ml of ethanol is added sufficient chloroform to dissolve the reactants. The pH is adjusted to between 7 and 9 and a 3 molar exces of 30% hydrogen peroxide in water is added dropwise at room temperature. The reactants are stirred for 5 hours after which sufficient ferrous sulfate is added to neutralize the excess peroxide. The mixture is then acidified with hydrochloric acid and the organic solvent evaporated off. The water solution remaining is made basic and extracted with chloroform. The chloroform is evaporated off yielding 3'-(4-pyridyl)-spiro[4-methyl-1,2,3,4-tetrahydronaphthalene-2,2'-oxirane]-1-one.

Following the procedure of step B of Example 1, the above 3'-(4-pyridyl)-spiro[4-methyl-1,2,3,4-tetrahydronaphthalene-2,2'-oxirane]-1- one is treated with hydrazine to yield 4,5-dihydro-5-methyl-3-(4-pyridyl)-2H-naphtho[1,2-c]pyrazole.

EXAMPLE 3

4,5-dihydro-5-methyl-3-4-pyridyl)-2H-naphtho[1,2-c]pyrazole

To a mixture of 25 grams of 2-(4-pyridylmethylene)-3,4-dihydro-4-methyl-1 (2H)-naphthalenone and 5 grams of hydrazine in 150 ml of ethanol is added sufficient chlorform to dissolve all the reactants. The solution is refluxed overnight under anhydrous conditions. After cooling, the reaction mixture is filtered and the solvent removed by evaporation to yield 5-methyl-3-(4-pyridyl)-3,3a,4,5-tetrahydro-2H-naphtho[1,2-c]Pyrazole. This is chromatographed on silica using benzene as the eluant to yield 4,5-dihydro-5-methyl-3l-(4-pyridyl)-2H-naphtho[1,2c]pyrazole.

Following the above procedure but using an equivalent amount of
  a. 2-(4-pyridylmethylene)-3,4-dihydro-3-methyl-1(2H)-naphthalenone;
  b. 22(4-pyridylmethylene)-3,4-dihydro-3,4-dimethyl-1(2H)-naphthalenone;
  c. 2-(4-pyridylmethylene)-3,4-dihydro-4,4-dimethyl-1(2H)-naphthalenone;
  d. 2-(p-chlorobenzylidene)-3,4-dihydro-4-methyl-1(Lb 2H)-naphthalenone or
  e. 2-benzylidene-3,4-dihydro-4-methyl-1(2H)-naphthalenone in place of the 2-(4-pyridylmethylene)-3,4-dihydro-4-methyl-1-(2H)-naphthalenone, there is obtained
  a. 4,5-dihydro-4-methyl-3-(4-pyaridyl)-2H-naphtho[1,2-c]pyrazole;
  b. 4,5-dihydro-4,5-dimethyl-Mb 3-(4-pyridyl)-2H-naphtho[1,2-c]pyrazole;
  c. 4,5-dihydro-5,5-dimethyl-3-(4-pyridyl)-2H-naphtho[1,2-c]pyrazole;
  d. 4,5-dihydro-5-methyl-3-(p-chlorophenyl)-2H-naphtho[1,2-c]Pyrazole or
  e. 4,5-dihydro-5-methyl-3-phenyl-2H-naphtho[1,2-c]pyrazole respectively.

EXAMPLE 4

4,5-dihydro-5-methyl-3-(4pyridyl)-2H-naphtho[1,2-c]pyrazole

Into a flask equiped with a magnetic stirring bar is charged 5.0 grams of the 5-methyl-3-(4-pyridyl)-3,3a,4,5-tetrahydro-2H-naphtho[1,2-c]pyrazole prepared as in example 3, 25 grams of activiated manganese dioxide and 150 ml of dry benzene. The mixture is stirred for about 12 hours at room temperature, after which the manganese salts are filtered off and the solvent removed in vacuo. The solid is crystallized from ethanol to yield 4,5-dihydro-2-methyl-3-(4-pyridyl)-2H-naphtho.[1,2-c]pyrazole.

EXAMPLE 5

4,5-dihydro-5-methyl-3-(4-pyridyl)-2H-naphtho[1,2-c]pyrazole.

A solution of 12.5 grams of 2-insonicotinoyl-4-methyl-α-tetralone and 2 1 grams of hydrazine in 50 milliliters of ethanol is refluxed for 1 hours. The solution is then acidified with 100 milliliters of 1N hydrochloric acid and extracted twice with 100 milliliteres of methylene chloride. The acueous solution is then made basic with sodium bicarbonate and extracted again with methylene chloride. The latter extractes are washed with water, dried and concentrated under vacuum. The 4,5dihydro-4methyl-3-(4-pyridyl)-Pb 2H-naphtho[1,2-c]pyrazole which precipitates is recrystallized from ethanol.
  a. 2-nicotinoyl-3-methyl-α-tetralone;
  b. 2-nicotinoyl-3,4-dimethyl-α-tetralone;
  c. 2-nicotinoyl-4,4-dimethyl-α-tetralone;
  d. 2-(p-chlorobenzoyl)-4-methyl-α-tetralone or
  e. 2-benzoyl-4-methyl-α-tetralone inplace of the 2-nicotinoyl-4-methyl-α-tetralone, there is obtained obtained
  a. 4,5-dihydro-4-methyl-3-(4-pyridyl)-2H-naphtho[1,2-c]pyrazole;
  c. 4,5-dihydro-5,5-dimethyl-3-(4-pyridyl)-2H-naphtho [1,2-c]pyrazole;
  d. 4,5-dihydro-5-methyl-3-(p-chloropheny)-2H-naphtho [1,2-c]pyrazole or
  e. 4,5-dihydro-5-methyl-3-phenyl-2H-naphtho [1,2-c]pyrazole respectively.

EXAMPLE 6

4,5-dihydro-5-methyl-3-(4-pyridyl)-2H-naphtho[1,2-c]pyrazole

Step A: 2-(4-pyridylmethylene)3,4-dihydro-4-methyl-1(2H)-naphthalenone

A mixture of 80.0 grams (0.50 moles) of α-tetralone, 64.2 grams (0.60 moles) of 4-pyridinecarboxaldehyde, 10 grams of piperidine and 10 grams of acetic acid are heated at 80° for 19 hours. The resultant solid is crystallized from about 400 ml. of ethanol to give 2-(4-pyridylmethylene)-3,4-dihydro-4-methyl-1(2H)-naphthalenone.

Step B: 4,5-dihydro-5-methyl-3-(4-pyridyl)-2H-naphtho[1,2-c]pyrazole

To 24.0 grams (0.1 oles) of the compound of Step A of this exampel in a flask equipped with stirrer and condenser are added 4.8 grams (0.15 Mole) of hydrazine hydrate (95%) and 150 ml. of isopropanol. The mixture is stirred and refluxed for about 24 hours and the solvent is then crystallized from methanol to given 4,5-dihydro-5-methyl-3-(4-pyridyl)-2h-naphtho[1,2-c]pyrazole.

What is claimed is:

1. A compound of the formula

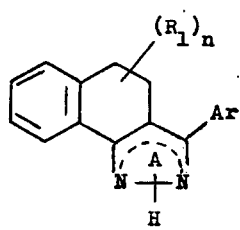

where
ring A has the structure

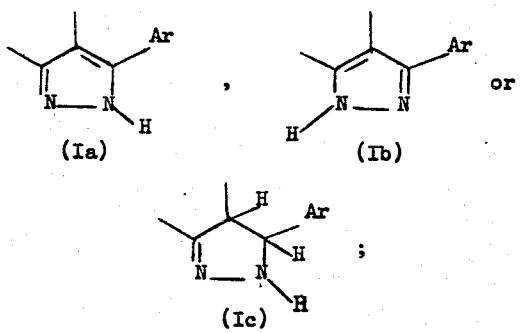

$n$ is 1 or 2
$R_1$ is straight chain lower alkyl of 1 to 4 carbon atoms and
Ar is

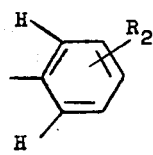

where $R_2$ represents hydrogen or halo having an atomic weight of about 19 to 36
or pharmaceutically acceptable acid addition salt thereof.

2. The compound of claim 1, which is 4,5-dihydro-5-methyl-3-(p-chlorophenyl)-2H-naphtho[1,2-c]pyrazole.

3. The compound of claim 1, which is 4,5-dihydro-5-methyl-3-phenyl-2H-naphtho[1,2-c]pyrazole.

* * * * *